United States Patent [19]
Stenzler

[11] Patent Number: 6,067,983
[45] Date of Patent: May 30, 2000

[54] METHOD AND APPARATUS FOR CONTROLLED FLOW SAMPLING FROM THE AIRWAY

[75] Inventor: Alex Stenzler, Anaheim Hills, Calif.

[73] Assignee: Sensormedics Corporation, Yorba Linda, Calif.

[21] Appl. No.: 08/934,175

[22] Filed: Sep. 19, 1997

[51] Int. Cl.[7] .................................................. A61M 16/00
[52] U.S. Cl. ................................ 128/204.23; 128/206.29
[58] Field of Search .......................... 128/201.18, 204.23, 128/205.19, 206.29; 600/532, 543

[56] References Cited

U.S. PATENT DOCUMENTS

| | | | |
|---|---|---|---|
| 3,658,058 | 4/1972 | Neidhart et al. | 128/201.18 |
| 3,910,261 | 10/1975 | Ragsdale et al. | 600/532 |
| 4,674,492 | 6/1987 | Niemeyer | 128/202.22 |
| 4,756,670 | 7/1988 | Arai | 600/532 |
| 4,832,042 | 5/1989 | Poppendiek et al. | 128/205.19 |
| 5,050,615 | 9/1991 | Malkamaki | 600/532 |
| 5,265,595 | 11/1993 | Rudolph | 128/204.23 |
| 5,398,695 | 3/1995 | Anderson et al. | 600/532 |
| 5,425,374 | 6/1995 | Veda et al. | 600/532 |
| 5,526,818 | 6/1996 | Ruismaki | 600/532 |
| 5,645,046 | 7/1997 | Kay | 128/201.18 |
| 5,676,131 | 10/1997 | Anderson et al. | 128/204.23 |
| 5,795,787 | 8/1998 | Silkoff et al. | 128/206.29 |

OTHER PUBLICATIONS

Philip E. Silkoff et al., Marked Flow–dependence of Exhaled Nitric Oxide Using a New Technique to Exclude Nasal Nitric Oxide, Am. J. Respir. Crit. Care Med., 155:260–67 (1997).

*Primary Examiner*—Aaron J. Lewis
*Attorney, Agent, or Firm*—Lyon & Lyon LLP

[57] ABSTRACT

An apparatus and method for controlled flow sampling from the airway includes a mouthpiece, or a connector attached to a tube inserted in the subject's trachea, either of which is used to capture gases from the subject's airway. Attached to the mouthpiece or the connector is a total airway occlusion. A pump or vacuum source, maintained at a lower pressure than the pressure inside the airway, is connected to the total airway occlusion, pulling gas out of the airway independent of the subject's volition. The flow is maintained at a substantially constant rate chosen by the operator through control over the source of low pressure. As gases flow out of the airway, they flow through a gas analyzer which measures desired properties of the gas.

8 Claims, 3 Drawing Sheets

METHOD AND APPARATUS FOR CONTROLLED FLOW SAMPLING FROM THE AIRWAY

BACKGROUND OF THE INVENTION

The invention relates generally to breath analysis, and more particularly to controlled flow sampling of gases from the airway.

The amount of nitric oxide (NO) exhaled through the airway functions as an important diagnostic indicator of pulmonary inflammation. In a normal, healthy person, the level of NO in the airway is in the range of 6–25 parts per billion (ppb). However, when the lungs are inflamed, as, e.g., when a person has asthma, NO levels can increase significantly to several hundred ppb.

The measurement of NO from the airway is highly flow-dependent. The production of NO from the airway is constant. Consequently, the measured concentration of NO in the expiratory flow will be less as the flow increases and the NO is diluted by the greater exhaled volume. Similarly, the measured concentration will be greater when the expiratory flow decreases and the NO level is increased relative to the lesser exhaled volume. Therefore, to make reliable and reproducible measurements of exhaled NO, the flow must be kept constant.

In addition, the nasal cavities normally produce elevated levels of NO. To accurately determine the level of NO produced by the lungs, it is necessary to avoid NO contamination from the nasal cavity. Exhalation pressure as low as 3.7 mmHg will close the soft palate and seal the nasal cavity from the airway.

Some existing tests for measuring pulmonary NO, such as, e.g., the single-breath nitrogen washout and single-breath diffusing capacity tests, utilize unsatisfactory flow control methods. Flow control methods used for these tests have included a visual display of the actual flow for the subject to match and restrictors to limit the flow.

The use of a visual display requires the subject to watch a pressure gauge or other device measuring the subject's exhalation pressure and use that pressure information to adjust his or her exhalation to match and maintain a constant exhalation pressure, thereby generating a constant outward flow rate. This method is unsatisfactory for several reasons. First, it cannot be used with test subjects who are incapable of perceiving the display, such as visually impaired or unconscious subjects. Second, it cannot be used with subjects who are unable to understand how to follow the procedure, such as very young children or subjects with Alzheimer's disease. Third, it is difficult for the subject to produce a substantially constant flow because the subject must continually adjust his or her exhalation pressure based on its deviation from the desired exhalation pressure, as indicated by the display.

The use of restrictors to limit the flow is also unsatisfactory. Silkoff et. al. have published a method for controlling expiratory flow that uses a high resistance needle to limit the flow to 46 ml/sec when the airway pressure is held at 20 mmHg. Philip E. Silkoff et. al., *Marked Flow-dependence of Exhaled Nitric Oxide Using a New Technique to Exclude Nasal Nitric Oxide*, Am. J. Respir. Crit. Care Med., 155:260–67 (1997), which is incorporated herein by reference. The subject inhales through a one-way valve system to maximum inspiration and then exhales against the resistor to maintain the 20 mmHg pressure for 10–20 seconds. Because this technique requires the subject to generate a positive pressure, it cannot be used with subjects who may be paralyzed or unable to generate a positive pressure to control the sampling flow rate, or subjects with a tube placed within the airway. Further, the Silkoff technique requires the subject to generate a 20 mmHg positive pressure, even though pressures as low as 3.7 mmHg will close the soft palate and seal the nasal cavity. In addition, because the subject must blow into the device of his or her own volition for up to 20 seconds, it is difficult to use with children because their limited attention span, especially when ill, can make it impossible to obtain a measurement.

Thus, conventional measurement techniques cannot be used to diagnose large segments of the patient population, i.e., small children, the unconscious, the paralyzed, those with Alzheimer's disease, the mentally ill, and others. Further, the visual feedback method does not consistently produce a substantially constant flow. It is apparent that a method and apparatus for measuring the exhaled concentration of gases from the airway that generates the required pressure and controls the flow independently of the subject, rather than relying on the patient's control of his or her own exhalation, is desirable.

SUMMARY OF THE INVENTION

The present invention provides a controlled flow sampling apparatus and method designed to satisfy the aforementioned needs. Accordingly, the present invention relates to apparatus and method for controlled flow sampling from the airway, which include the steps of: (1) collecting gases from the airway; (2) maintaining a positive pressure in the oral cavity of the subject to seal the soft palate, when a mouthpiece is used for collecting gases from the airway; (3) generating a pressure lower than that of the airway to produce a flow out of the airway; (4) maintaining a substantially constant flow rate; and (5) measuring the composition of the gas removed from the airway.

In a first aspect of the invention, a mouthpiece or a connection to a tube inserted in the patient's trachea may advantageously be used to capture gases from the subject's airway. In a second, separate aspect of the invention, reduced pressure may advantageously be generated by devices including, but not limited to, a pump. Preferably, a substantially constant flow rate is maintained at the level set by the operator by a control mechanism associated with the pressure generating device, such as, e.g., an electrical speed control on the pump.

DETAILED DESCRIPTION OF THE PREFERRED EMBODIMENTS

Figure 1:
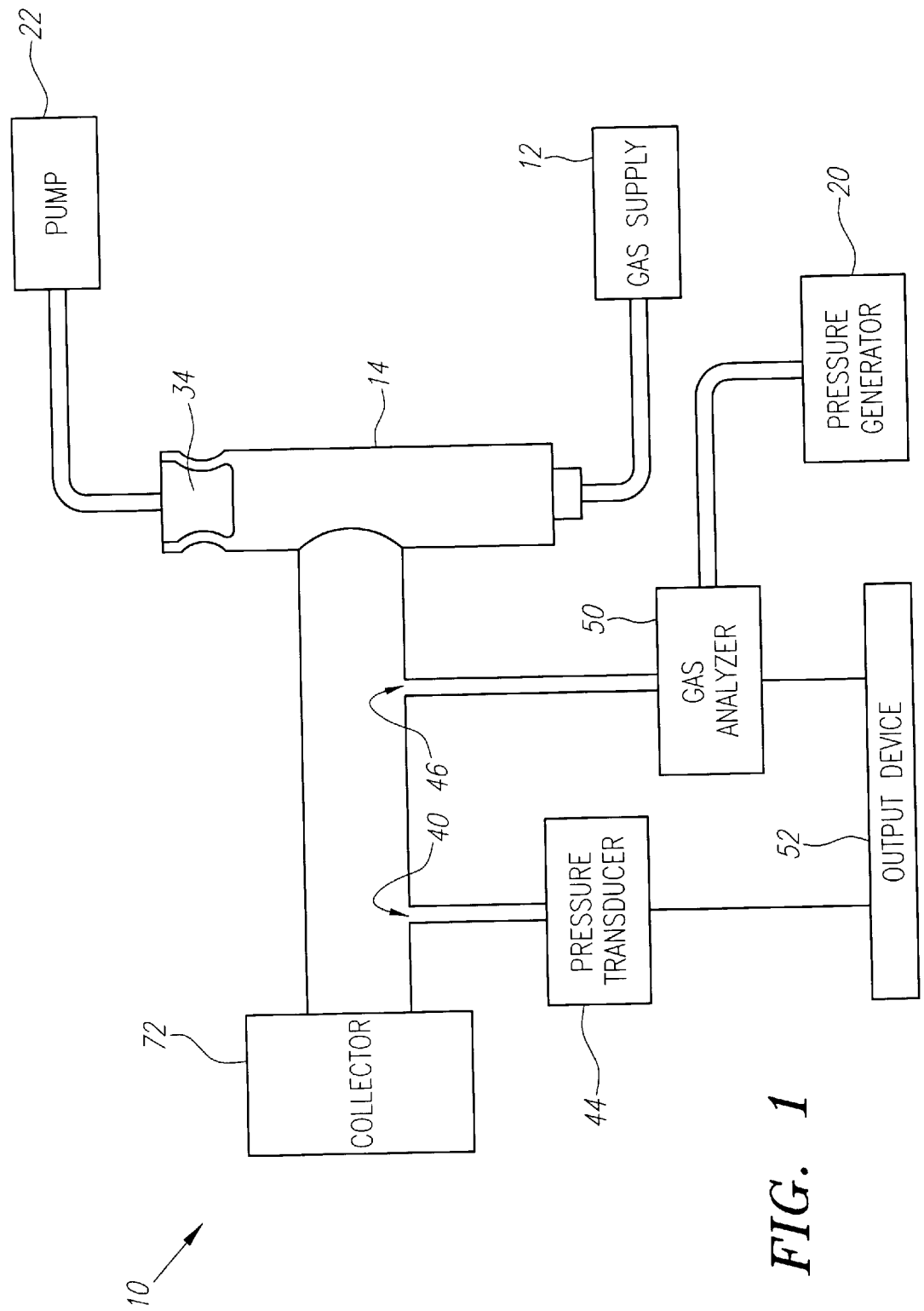
FIG. 1 is a schematic diagram of an apparatus for controlled flow sampling from the airway.

Referring now to the drawings, and more particularly to FIG. 1, there is shown apparatus, generally designated 10, for obtaining a controlled flow from a subject's airway and analyzing gases contained within that flow. The subject's airway includes the lungs and trachea. In a particular embodiment, the apparatus 10 advantageously includes a gas supply 12 for providing gas of known composition for the subject to inhale; a collector 72 for capturing gas flow out of the subject's airway; a total airway occlusion 14 for introducing gas provided by the gas supply 12 into the subject through a collector 72 and receiving gas flow out of the subject's airway through the collector 72; a pump 22 to inflate a one-way valve 34 to block exhalation by the subject; a transducer port 40 leading to a pressure transducer 44 for measuring the exhalation pressure of the subject; an analyzer port 46 leading to a gas analyzer 50 for analyzing the contents of that flow; an output device 52 for recording or displaying measurements from the pressure transducer 44 and the gas analyzer 50; and a pressure generator 20 for generating a lower pressure than that of the subject's airway to produce a substantially constant flow rate through the total airway occlusion 14.

Figure 2:
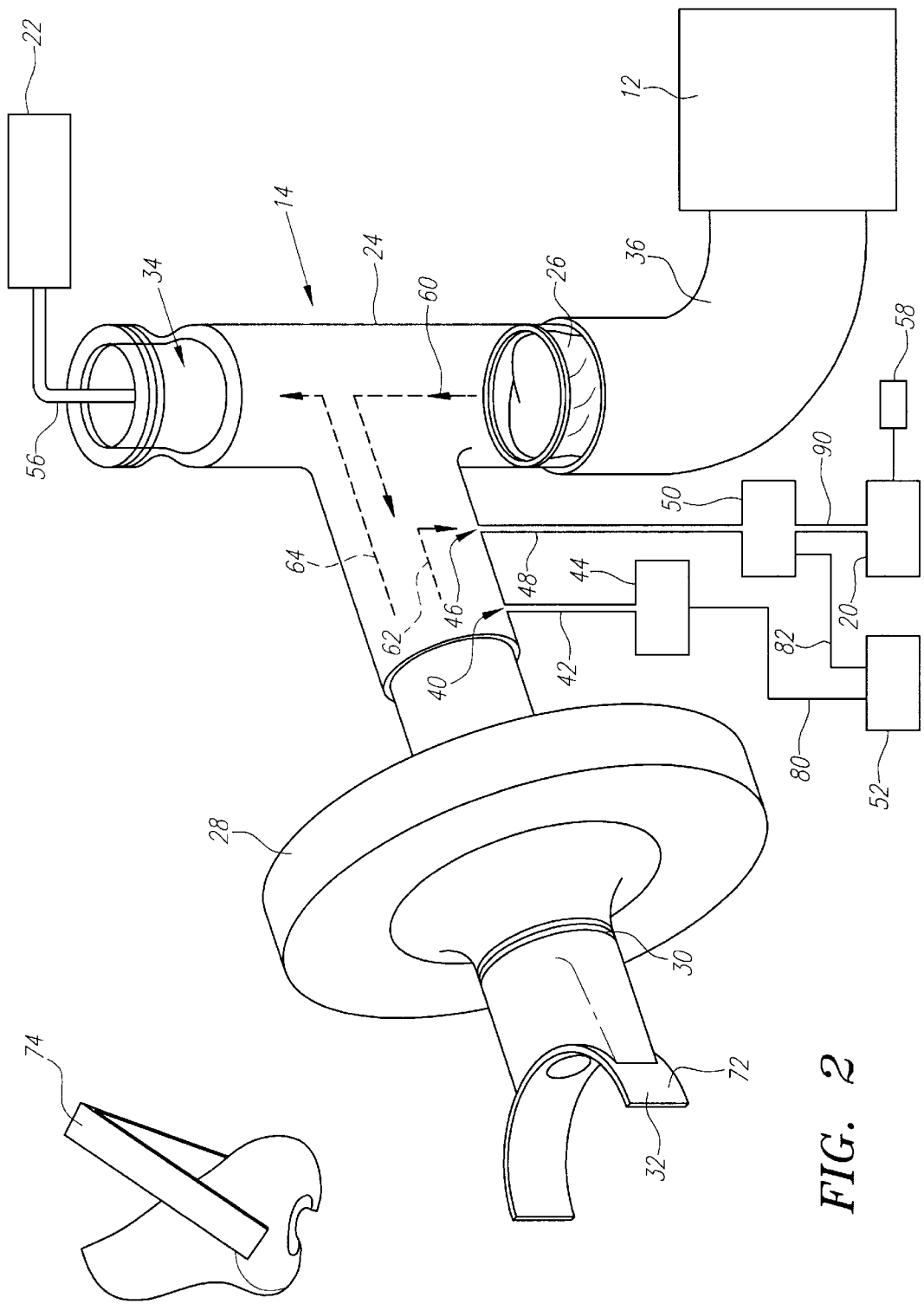
FIG. 2 is a schematic cross-sectional view of a housing that can be used in the apparatus of FIG. 1.
Figure 3:
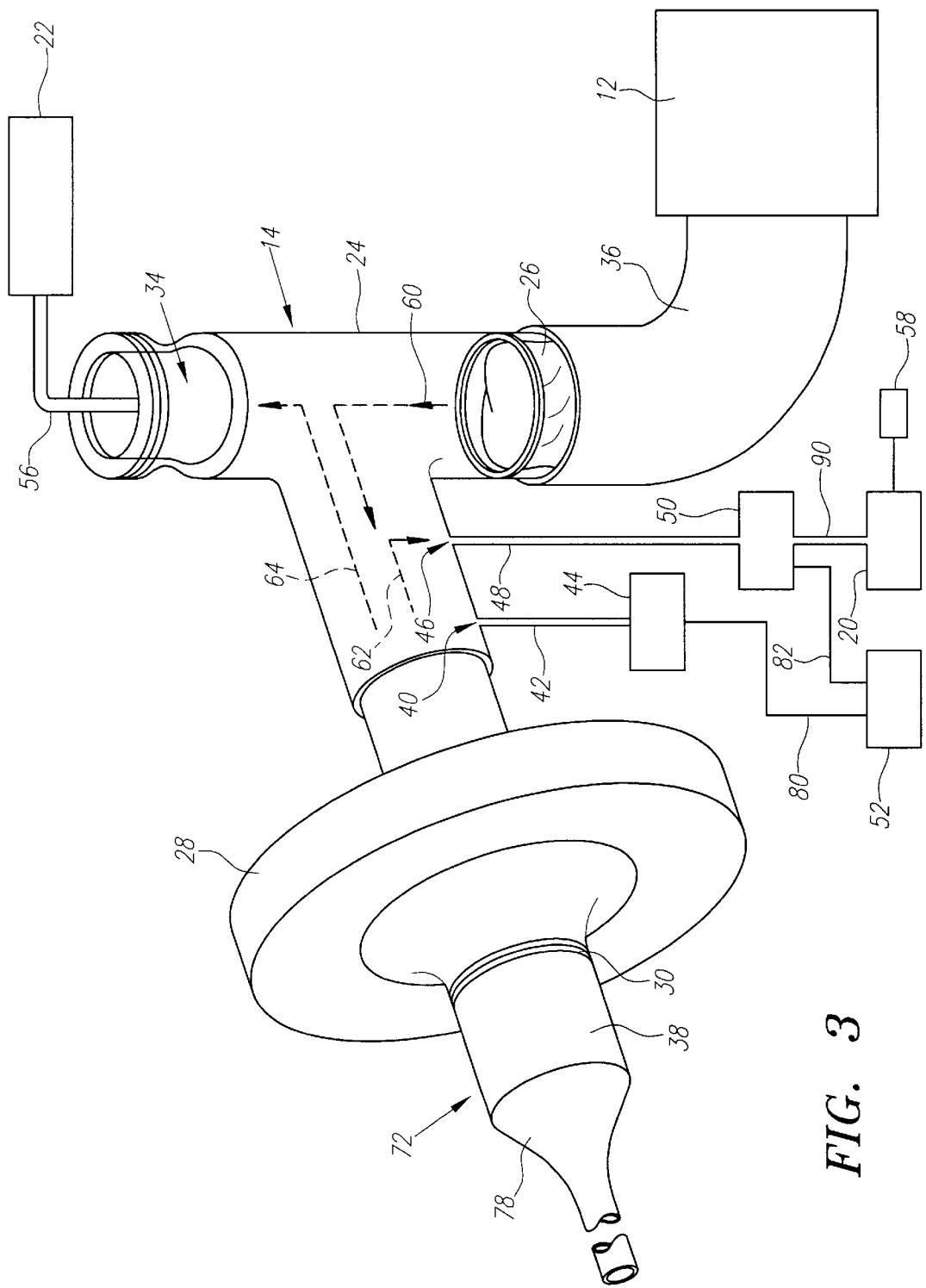
FIG. 3 is a schematic cross-sectional view of an alternate embodiment of a housing suitable for use in the apparatus of FIG. 1.

In the embodiments of FIGS. 2 and 3, the gas supply 12 contains gases of known composition. A supply hose 36 connects at one end to the gas supply 12 and at the other end to the total airway occlusion 14, enabling the introduction of gas from the gas supply 12 into the subject. Preferably, the gas supply 12 is a gas tank, but the gas supply 12 may be any device capable of providing adequate quantities of gas of known composition, such as, e.g., a balloon. The connectors between the supply hose 36 and the gas supply 12 at one end, and between the supply hose 36 and the total airway occlusion 14 at the other end, may be any connectors capable of maintaining a pressure seal against leakage either into or out of the apparatus 10.

Also, as shown in FIGS. 2 and 3, the total airway occlusion 14 for introducing gas into the subject and capturing gas flow out of the subject preferably includes a housing 24, a first one-way valve 26, a filter 28, a connector 30, and a second one-way valve 34. The total airway occlusion 14 prevents the subject from inhaling ambient air which may contain contaminants. The total airway occlusion 14 also prevents the subject from exhaling when both the first one-way valve 26 and the second one-way valve 34 are closed, and ensures that substantially all of the subject's expiratory flow is drawn out of the subject by the pressure generator 20. The housing 24 contains the first one-way valve 26, the second one-way valve 34, and the connector 30. The housing 24 prevents atmospheric gases from leaking into the total airway occlusion 14 and contaminating the flow to be sampled. The supply hose 36 connects to total airway occlusion 14 at the first one-way valve 26. The transducer port 40 allows gas to pass out of the total airway occlusion 14 through a hose 42 to a pressure transducer 44. The analyzer port 46 allows gas to pass out of the total airway occlusion 14 through a hose 48 to the gas analyzer 50. Preferably, the total airway occlusion 14 includes the filter 28, but the filter 28 need not be used for the total airway occlusion 14 to function adequately. A collector 72 attaches to the total airway occlusion 14 at the connector 30.

In a particular embodiment shown in FIG. 2, the collector 72 is a mouthpiece 32. The subject places the mouthpiece 32 on or against his or her mouth, creating a seal. The mouthpiece 32 prevents the subject from inhaling ambient air and captures substantially all of the subject's expiratory flow. Any mouthpiece compatible with the connector 30 that forms a seal with the subject's mouth may be used. When the mouthpiece 32 is used, a nasal block 74 is also used to protect gas from the gas supply 12 from contamination with or displacement by ambient air inhaled by the subject. Preferably, the nasal block 74 is a clip, but any device capable of preventing ambient air from entering the nasal cavity, such as, e.g., plugs, may be used. Without the nasal block 74, the subject could inhale ambient air of unknown composition through his or her nose, rendering the subsequent measurements of outward flow 62 inaccurate.

In an alternate embodiment shown in FIG. 3, the collector 72 is a tracheal tube adaptor 38. The tracheal tube adaptor 38 connects to a tube 78 that has been inserted into the trachea of the subject, thereby allowing sampling of the outward flow 62 from an intubated patient that could not use the mouthpiece. The tracheal tube adaptor 38 preferably attaches to the housing 24 at the connector 30. Nose clips are not needed in this embodiment because the tube provides air directly to and removes air directly from the airway, bypassing the nasal cavity and the contamination it may cause. Further, because the nasal cavity is bypassed, the subject need not generate a 3.7 mmHg exhalation pressure to seal the soft palate and close off the nasal cavity from the airway.

In the embodiments of FIGS. 2 and 3, during inhalation, the first one-way valve 26 opens to allow gases 60 provided through the supply hose 36 from the gas supply 12 to enter the housing 24 and then pass through the collector 72 into the airway of the subject. The second one-way valve 34 is closed when the subject is inhaling gases from the gas supply 12 through the housing 24, to prevent inhalation of ambient air. Preferably, the second one-way valve 34 is a balloon valve, but another type of one-way valve, such as, e.g., a sliding or rotating valve, may be used. Preferably, pump 22 inflates the second one-way valve 34 through the hose 56, which is connected to pump 22 at one end and to the second one-way valve 34 at the other.

After the subject has completed inhalation, the first one-way valve 26 closes to prevent flow from the subject's airway from traveling back into the gas supply 12 and to prevent gases from the gas supply 12 from entering the housing 24 and diluting the flow to be sampled from the subject. With both the first one-way valve 26 and the second one-way valve 34 closed, the total airway occlusion 14 blocks exhalation by the subject. As the subject attempts to exhale, pressure increases in the total airway occlusion 14. The subject must generate at least 3.7 mmHg pressure in order to seal the soft palate and prevent air from the nasal cavity from contaminating the expiratory flow. The 3.7 mmHg pressure is less than standard human exhalation pressure, and therefore is generated in the normal course of breathing. The pressure transducer 44 measures the pressure generated by the subject in the total airway occlusion 14 with both the first one-way valve 26 and second one-way valve 34 closed. Gas in the total airway occlusion 14 communicates with the pressure transducer 44 through the transducer hose 42, enabling the pressure transducer 44 to measure the pressure within the total airway occlusion 14. One end of the transducer hose 42 attaches to the total airway occlusion 14 at the transducer port 40, and the opposite end of the transducer hose 42 attaches to the pressure transducer 44. Preferably, the transducer hose 42 is a flexible hose, but a rigid pipe may be used. The pressure transducer 44 is connected to the output device 52 by transducer wiring 80. The pressure transducer 44 sends through transducer wiring 80 to the output device 52 a digital or analog signal indicating the pressure that the pressure transducer 44 is measuring. Transducer wiring 80 is connected to the pressure transducer 44 at one end and to the output device 52 at its other end. When the output device 52 indicates that the subject is generating a pressure greater than 3.7 mmHg in the total airway occlusion 14, a pressure generator 20 is activated.

Preferably, the pressure generator 20 is controlled manually by the operator, but it may also be controlled automatically, such as, e.g., by a signal from the output device to activate when the pressure in the total airway occlusion 14 has reached 3.7 mmHg. The pressure generator 20 generates a pressure lower than that within the airway of the subject. Preferably, the pressure generator 20 is a pump, which should be of sufficient size to generate a low enough pressure to create an outward flow 62 out of the subject's airway. However, a vacuum source or other source of low pressure may be used. The amount of pressure generated by the pressure generator 20 is controlled by the operator by a regulator 58. The operator uses the regulator 58 to preset the pressure generated by pressure generator 20 and thereby create a substantially constant outward flow 62 from the subject. Preferably, the regulator 58 controls the amount of pressure generated by the preferred embodiment, that is, a pump, by electronic speed control of the pump motor, but any other mechanism whereby a substantially constant flow rate can be maintained at a desired level may be used. If a pressure generator 20 other than a pump is used, the regulator 58 may take the form of a flow restrictor placed between the pressure generator 20 and the outlet hose 56, but any other mechanism whereby a substantially constant flow rate can be maintained at a desired level may be used.

A pressure generator hose 90 attaches at one end to the pressure generator 20 and at the other end to the gas analyzer 50. In turn, the gas analyzer 50 is connected to one end of an analyzer hose 48. The other end of the analyzer hose 48 connects to the total airway occlusion 14 at the port 46, forming a path for the gas to communicate between the total airway occlusion 14 and the pressure generator 20.

In the embodiment of FIG. 3, the pressure transducer 44 is not used. The subject need not generate any minimum pressure.

With the pressure generator 20 activated, an outward flow 62 from the airway of the subject begins. The pressure generator 20 controls the outward flow 62, maintaining a substantially constant flow rate. The subject cannot exhale of his or her own volition while the pressure generator 20 controls the outward flow 62.

The outward flow 62 travels through the analyzer port 46 and the analyzer hose 48 to the gas analyzer 50. Preferably, the gas analyzer 50 measures the concentration of nitric oxide in the outward flow 62, but other measurements may be made as well. Preferably, the gas analyzer 50 converts the measurements it makes into digital form, but it may convert them into analog form as well. The gas analyzer 50 then transmits those measurements through analyzer wiring 82 to the output device 52. The analyzer wiring 82 is connected to the gas analyzer 50 at one end and to the output device at its other end. Preferably, the output device 52 is a computer, but other types of output device may be used, such as, e.g., a data recorder. The operator then reads the desired measurements from the output device 52.

After the outward flow 62 has passed through the gas analyzer 50, it passes through the pressure generator hose 90 and then to the pressure generator 20, where the outward flow 62 is vented or retained. The pressure generater hose 90 is connected at one end to the gas analyzer 50 and at the other end to the pressure generator 20.

As shown in FIGS. 2 and 3, when the test is complete, the second one-way valve 34 then opens. Preferably, a pump 22 deflates the second one-way valve 34 through the hose 56. The hose 56 is connected at one end to the pump 22 and at the other end to the second one-way valve 34. Preferably, the second one-way valve 34 is under manual operator control, but it may be controlled automatically, such as, e.g., by electronic signals from the pressure transducer or the output device. After the second one-way valve 34 has been opened, an outward flow 64 may exit the total airway occlusion 14 through the second one-way valve 34.

A preferred controlled flow airway sampling apparatus and method and many of its attendant advantages have thus been disclosed. It will be apparent, however, that various changes may be made in the form, construction, and arrangement of the parts without departing from the spirit and scope of the invention, the form hereinbefore described being merely a preferred or exemplary embodiment thereof. Therefore, the invention is not to be restricted or limited except in accordance with the following claims.

I claim:

1. An apparatus for controlled flow sampling of gases from a living subject's airway, comprising:

(a) a gas supply;

(b) a total airway occlusion which receives gas from said gas supply;

(c) a collector connected to said total airway occlusion, for transferring gas received by said total airway occlusion from said gas supply to such a living subject and for capturing gases from such a living subject's airway;

(d) a pressure generator which generates a pressure lower than that of such a living subject's airway and which is connected to said total airway occlusion to produce a substantially controlled gas flow rate from such a living subject's airway;

(e) a regulator for setting the pressure produced by said pressure generator;

(f) a pressure transducer which measures the pressure generated by such a living subject in said total airway occlusion when said total airway occlusion blocks exhalation;

(g) a gas analyzer which measures properties of the gases collected from such a living subject's airway; and (h) a display which outputs the data collected from said gas analyzer.

2. The gas analysis apparatus of claim 1, wherein said collector comprises a mouthpiece, said gas analysis apparatus further comprising a nasal block.

3. The gas analysis apparatus of claim 1, wherein said collector comprises a tracheal tube adaptor.

4. The gas analysis apparatus of claim 1, wherein said pressure generator comprises a pump.

5. The gas analysis apparatus of claim 1, wherein said pressure generator comprises a vacuum source.

6. An apparatus for controlled flow sampling of gases from a living subject's airway, comprising:

a mouthpiece adapted for insertion into the mouth of such a living subject, the mouthpiece allowing for the passage of gases therethrough into and out of the airway of such a living subject;

a nasal block adapted for attachment to such a living subject such that the nasal block substantially blocks the nostrils of such a living subject;

a pressure transducer in flow communication with the mouthpiece;

a pressure generator connected to the pressure transducer and in flow communication with the mouthpiece the pressure generator adapted to generate a pressure lower than the pressure of a living subject's airway to create and control an outward flow from the living subject's airway independent of the living subject's volition; and a gas analyzer in flow communication with the pressure generator and the mouthpiece, the gas analyzer receiving substantially all of the outward flow from the living subject's airway and adapted to measure properties of the gases removed from the airway of such a living subject through the mouthpiece.

7. A method for controlled flow sampling of gases from a living subject's airway, comprising:

inserting a mouthpiece into the mouth of a living subject;

providing breathable gas of known composition to the living subject;

monitoring such a living subject's exhalation pressure to ensure it remains above approximately 3.7 mmHg for sealing the soft palate of a living subject;

generating a pressure outside the mouthpiece lower than the pressure within such a living subject's airway to create and control and outward flow from the living subject's airway independent of the living subject's volition;

measuring the properties of the gas induced outward from such a living subject's airway.

8. The method of claim 7, further comprising the step after the inserting a mouthpiece step of blocking such a living subject's nostrils substantially completely.

* * * * *